(12) United States Patent
Wittmer et al.

(10) Patent No.: US 7,196,524 B2
(45) Date of Patent: Mar. 27, 2007

(54) SENSOR PLUG-IN HEAD, PARTICULARLY FOR A POTENTIOMETRIC SENSOR AND POTENTIOMETRIC SENSOR COMPRISING A SENSOR PLUG-IN HEAD

(75) Inventors: Detlev Wittmer, Maulbronn (DE); Wolfgang Babel, Weil der Stadt (DE)

(73) Assignee: Endress + Hauser Conducta Gesellschaft fur Mess-u. Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 10/537,541

(22) PCT Filed: Nov. 26, 2003

(86) PCT No.: PCT/EP03/13274

§ 371 (c)(1),
(2), (4) Date: Nov. 30, 2005

(87) PCT Pub. No.: WO2004/051246

PCT Pub. Date: Jun. 17, 2004

(65) Prior Publication Data

US 2006/0125484 A1 Jun. 15, 2006

(30) Foreign Application Priority Data

Dec. 3, 2002 (DE) .................. 102 56 649

(51) Int. Cl.
 G01R 29/12 (2006.01)
 G01N 27/26 (2006.01)
(52) U.S. Cl. .................. 324/458; 204/435; 204/433
(58) Field of Classification Search ................ 324/458
See application file for complete search history.

(56) References Cited

U.S. PATENT DOCUMENTS

| | | | | |
|---|---|---|---|---|
| 4,444,644 A | * | 4/1984 | Hiramoto et al. | 204/406 |
| 5,820,739 A | * | 10/1998 | Graser et al. | 204/421 |
| 5,980,712 A | * | 11/1999 | Tauber et al. | 204/435 |
| 6,423,197 B1 | * | 7/2002 | Lenferink et al. | 204/408 |
| 6,551,478 B1 | * | 4/2003 | Bielawski et al. | 204/433 |

* cited by examiner

*Primary Examiner*—Andrew H. Hirshfeld
*Assistant Examiner*—Jeff Natalini
(74) *Attorney, Agent, or Firm*—Bacon & Thomas PLLC

(57) ABSTRACT

For simplified supply of potentiometric sensors with a reference electrolyte, a sensor plug head for connecting to a cable connection piece of a potentiometric sensor is provided. The sensor plug head including, besides the usual electric connections, a supply connection for connecting to a reference container of the potentiometric sensor. The supply connection includes, preferably, an electrolyte line and the reference container an opening, with the electrolyte line being connectable to the opening, in order to supply the reference container with electrolyte.

7 Claims, 3 Drawing Sheets

SENSOR PLUG-IN HEAD, PARTICULARLY FOR A POTENTIOMETRIC SENSOR AND POTENTIOMETRIC SENSOR COMPRISING A SENSOR PLUG-IN HEAD

FIELD OF THE INVENTION

The present invention relates to sensors requiring a liquid substance as a reference or calibration solution. To these sensors belong, for example, potentiometric sensors, especially pH-sensors or redox sensors, which will be used as examples in the following, although the invention is not to be limited to these examples.

BACKGROUND OF THE INVENTION

Especially, the present invention relates to a sensor head for a potentiometric sensor. Potentiometric sensors usually measure the potential difference between a working electrode and a reference electrode, with the working electrode being arranged in a buffer solution, which is separated by a glass membrane from the medium to be investigated. The reference electrode is arranged in a reference electrolyte—in the case of a pH-sensor e.g. in a 3.5 molar KCl solution.

In order to assure a constant quality of measurement, the reference electrolyte must be renewed on an appropriate schedule. To this end, pH and redox sensors usually have a replenishment opening on their lateral surface. The replenishment of the reference electrolyte proves to be cumbersome, in that operating personnel must search-out each sensor, in order to perform a filling through the replenishment opening.

SUMMARY OF THE INVENTION

An object of the present invention is, therefore, to provide a redox sensor, or components thereof, requiring a reduced effort for the replenishment of the reference electrolyte.

The object is achieved according to the invention by the plug head .

The sensor plug head of the invention, for connecting to a sensor having an output for issuing a measurement signal and having an liquid container fillable with a reference liquid or a calibration liquid, includes at least one input for receiving the measurement signal, with the sensor plug head further including a supply connection for connection to the liquid container.

The supply connection of the invention serves for supplying the liquid container with the electrolyte.

BRIEF DESCRIPTION OF THE DRAWINGS

Further advantages and perspectives of the invention are contained in the dependent claims, the description of the examples of embodiments, and the drawings, the figures of which show as follows:

DETAILED DESCRIPTION

Figure 1:
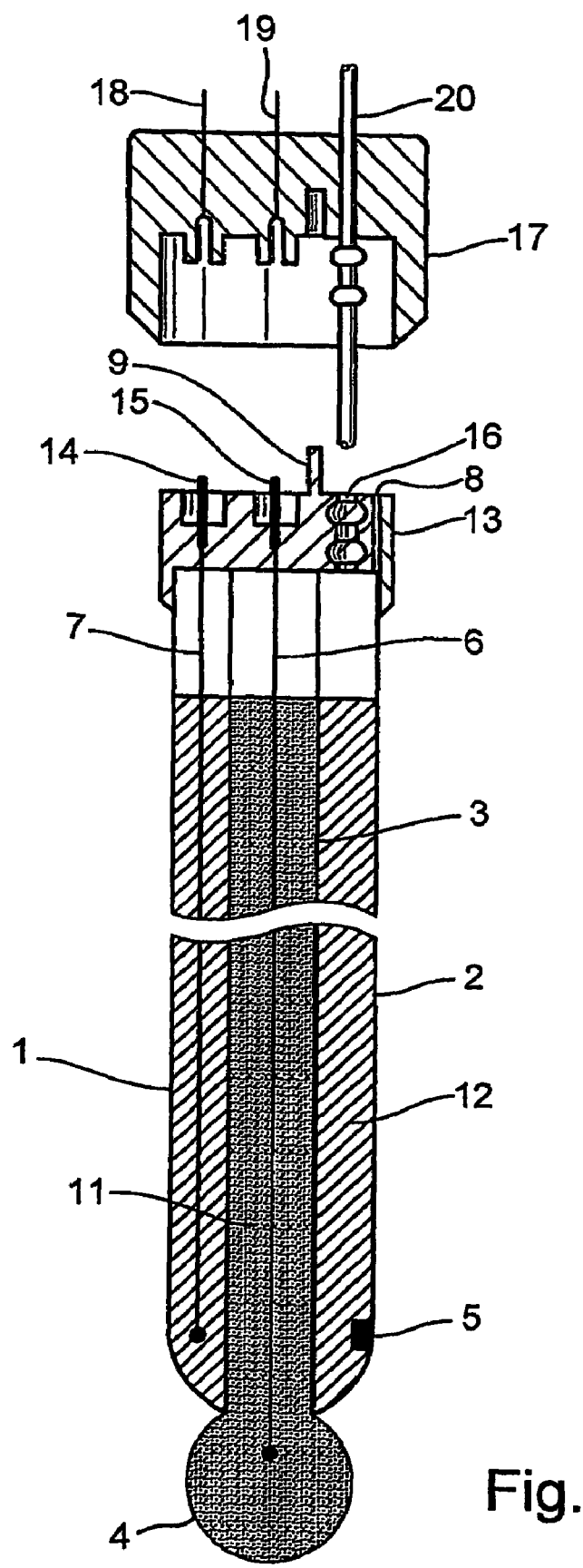
FIG. 1 is a longitudinal section through a first example of an embodiment of the plug head of the invention and a pH-electrode of the invention, with galvanic contacts and an opening on an end face of the reference container.

In the context of potentiometric sensors, the sensor plug head of the invention includes, for connecting to a potentiometric sensor for the output of a potential-dependent signal, in the case where the potentiometric sensor has a reference container, which is fillable with an electrolyte, at least one input for receiving the potential-dependent signal and a supply connection for connecting to the reference container. The supply connection of the invention serves for supplying the reference container with the electrolyte. The supply connection includes, preferably, a first connection element, and the reference container includes a second connection element, with the first connection element being complementary to the second connection element, i.e. producing a flow connection between the supply connection and the reference container, over which the reference container can be supplied with the electrolyte.

Preferably, the supply connection, or the first connection element, includes an electrolyte line, and the reference container, or the second connection element, includes an opening, with the electrolyte line being connectable to the opening, for supplying the reference container with electrolyte.

The invention will be explained in the following using the example of pH-sensors and plug heads for pH-sensors, but the explanations are readily adaptable by those skilled in the art for other potentiometric sensors and their plug heads.

The input for receiving a potential-dependent signal can, on the one hand, have galvanic contacts for the sampling of the working potential and the reference potential. Currently preferred, however, are forms of embodiment, in which a galvanic separation is present between the output of the pH-sensor and the input of the plug head. Preferably, the sensor plug head and the pH-sensor each have, for this purpose, mutually complementary, inductive interfaces, via which data exchange between sensor plug head and pH-sensor, and the power supply of the pH-sensor, take place. Details for the manufacture of inductive interfaces are disclosed, for example, in the European Patent Application No. 011124304 of the present assignee. The advantage of a non-galvanic, signal and power transfer, or transmission, lies, among other things, in the fact that all surfaces of the plug head and the complementary cable connection piece of the pH-sensor can be of a corrosion-resistant material. In a currently preferred form of embodiment with an inductive interface, the electrolyte line lies in the immediate vicinity of the inductive couplers. This is without problem, in so far as the plug head and the cable connection piece have exclusively corrosion-resistant surfaces, which are not affected by the reference electrolyte.

Of course, the electrolyte line can be placed in the immediate vicinity of the electric contacts also in the case of a plug head with galvanic coupling, but, in this case, greater care is required during the applying and removing of a plug head in order that a contamination of the contacts with the electrolyte be avoided. Additionally, barriers can be provided on the plug head, or cable connection, between the opening and the signal output, which barriers assure that contaminations of the surroundings of the opening by the electrolyte remain limited.

Both for the variants with galvanically separated transfer and for those with galvanic coupling, the invention includes a form of embodiment, in which the plug head exhibits a bayonet connection, by means of which it can be secured on the sensor. For this form of the invention, it is advantageous, that the electrolyte line, or the supply connection, be placed coaxially with the rotational axis of the bayonet connection.

In a further, preferred form of embodiment, the supply connection, or the electrolyte line, is placed in the edge region of the plug head. In this case, the electrolyte line is provided with a flexible connection end, which is connectable to a replenishment opening on the lateral surface of a conventional pH-electrode.

The supply connection, or electrolyte line, is connectable with a reservoir and, as required, suitable metering means, for enabling a filling of the reference container from a distance. Preferably, the filling can occur automatically, with both periodic and condition-dependent fillings being possible.

The electrolyte line can be in the form of a double line, with one conduit being for the filling of the reference container and a second conduit serving for pressure equalization or emptying of the reference container. The emptying of the reference container enables a complete exchange of the electrolyte, for which purpose, the reference container can, for example, be blown out, by introducing a gas through the first conduit of the electrolyte line into the reference container. The exchange of the electrolyte is more complete, the more the second conduit of the electrolyte line extends down into the reference container. To this end, the second conduit can either itself be made sufficiently long, or it can be connected to the upper opening of a capillary tube, which is arranged in the reference container and extends down to the lower end.

Of course, even a continuous exchange of the electrolyte may be used, in which, periodically, small amounts of electrolyte are added, with a portion of the already present electrolyte being expelled via the second conduit of the electrolyte line.

The electrolyte line should, preferably, be made of a non-corrosive material, or at least the surfaces, which come in contact with the electrolyte, should have a corrosion-resistant coating. Possible materials include, especially, polymeric materials and glass, with the polymeric materials and glass being combinable.

The supply line provided for supplying the reference container with electrolyte can be run either separately from the lines for the data exchange or power supply, or they can be integrated with the latter in a single cable. The integrated cable offers, among others, the advantage that the effort for laying the lines required for a sensor is significantly reduced.

Figure 2:
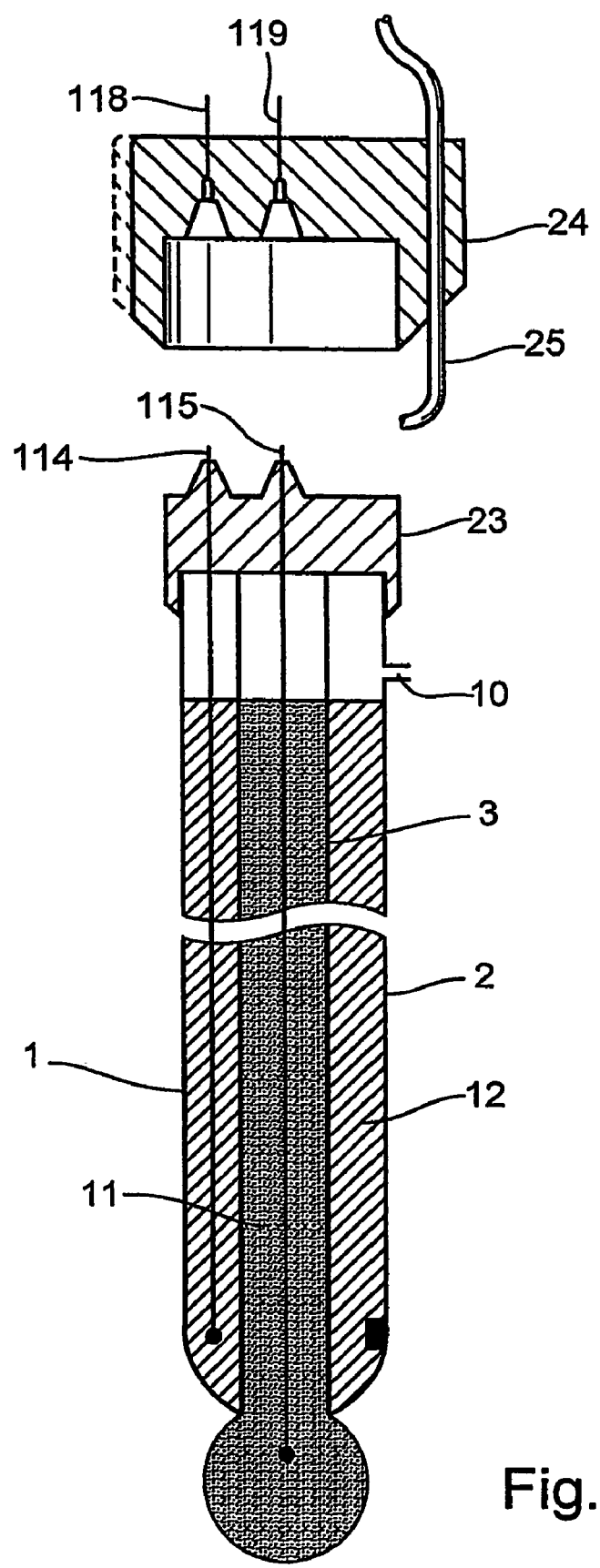
FIG. 2 is a longitudinal section through a second example of an embodiment of a plug head in a pH-electrode with a container opening on the lateral surface of the electrode.
Figure 3:
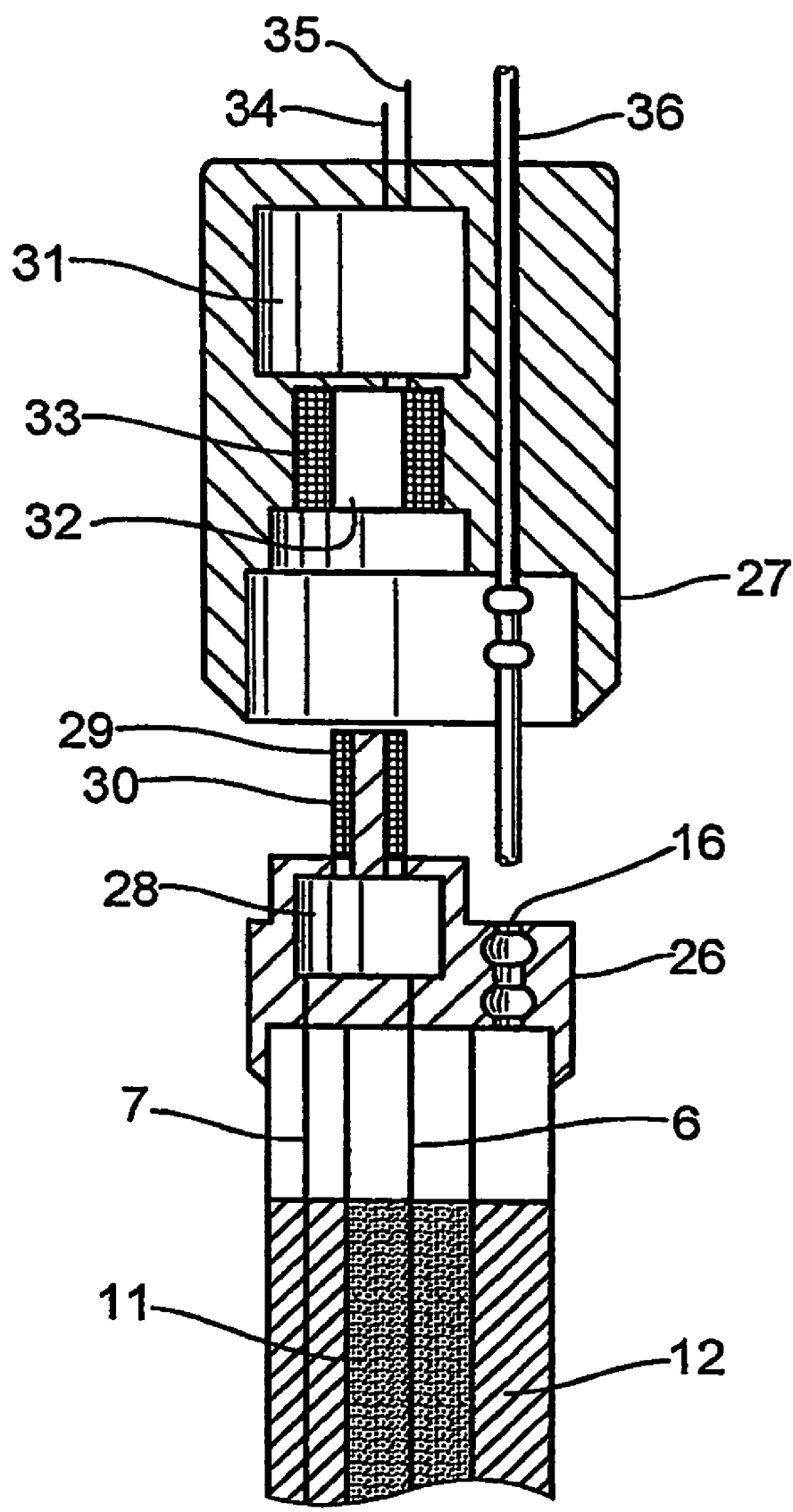
FIG. 3 is a detail view of a longitudinal section through another example of an embodiment of a plug head of the invention and a pH-electrode of the invention, with inductive signal transfer between the plug head and the pH-electrode.

The examples of embodiments in FIGS. 1–3 put the teachings of the invention into practice using customary glass electrodes, so-called "combination electrodes". A pH-electrode 1 includes, customarily, two coaxial glass tubes, namely the outer shell 2 and the inner shell 3. The outer shell 2 tapers at its lower end and is sealed there to inner shell 3, so that an outer container for an electrolyte 12 is formed between the outer shell and the inner shell. Arranged at the lower end of the inner shell is a glass membrane, mostly spherically shaped and having a wall thickness of less than one, up to a few, micrometers. The inner container, which is bounded by the inner shell 3 and the glass membrane 4, is filled with a buffer solution 11. Also arranged in the outer shell is a diaphragm 5, via which an electrolyte bridge to the medium to be analyzed is formed. Arranged in the inner container is the working electrode 6, which extends from the interior of the space surrounded by the membrane 4 up to the cable connection piece 13; 23; 26. Arranged in the outer container, or reference container, is a reference electrode 7, which extends from a lower section of the reference container, for example the level of the diaphragm 5, up to the cable connection piece 13; 23; 26.

Connectable to the cable connection piece is a plug head 17; 24; 27, which, on the one hand, has an input for read-out of the potentials of the working electrode and the reference electrode, or a corresponding signal, and which, according to the invention, additionally provides an electrolyte line, in order to supply the reference container through an appropriate opening with an electrolyte.

In the example of an embodiment presented in FIG. 1, the cable connection piece has an essentially sectionally cylindrical structure and is made of a polymeric material. Arranged in the end face of the cable connection piece 13 facing away from the pH-electrode are a reference connection 14 and a working connection 15, which are conductively connected, respectively, with the reference electrode 7 and the working electrode 6.

Furthermore, extending through the end surface of the cable connection piece 13 is a bore 16, which serves as replenishment opening for the electrolyte and which is aligned with the outer container situated between the inner shell 3 and the outer shell 2. The plug head 17 has a structure complementary to the cable connection piece, i.e. it includes a reference line 18 and a working line 19, whose connections make galvanic contact with the reference connection 14 and with the working connection 15, when the plug head 17 is plugged onto the cable connection piece 13. Moreover, the plug head provides an electrolyte line 20, which aligns with the replenishment opening and extends through this into the reference container, when the plug head 17 is plugged onto the cable connection piece 13.

The electrolyte line can (as shown in FIG. 1) have sealing elements on its lateral surface, which engage with complementary recesses in the replenishment opening 16 and, in this way, seal the opening 16. For this case, the form of embodiment shown in FIG. 1 is provided with an air-escape capillary 8, which enables an equalization of pressure between the electrolyte chamber and the environment. Instead of the capillary 8, also a two-conduit electrolyte line 20 can be provided, with the first conduit serving for the filling of the reference container and the second conduit serving for pressure equalization, or emptying of the reference container, as the case may be, as was discussed above. Finally, sealing means between the electrolyte line 20 and the replenishment opening 16 can be omitted and the diameter of the electrolyte line 20 can be so selected relative to the diameter of the replenishment opening 16, that a gap remains between the electrolyte line and the replenishment opening, for the purpose of enabling the pressure equalization.

A further aspect of the invention concerns the corrosion protection of the electric connections. In so far as the electrolyte feed now occurs in the immediate vicinity of the metal contacts, there is an increased danger of corrosion, since the contacts are exposed to a certain risk of contamination during the plugging of the plug head 17 and during its removal.

This is true especially for the reference connection 14 and the working connection 15 in FIG. 1, since these are arranged in recesses in the end face of the cable connection piece 13. This geometry is not ideal as concerns susceptibility to corrosion, since electrolyte, once having penetrated into the recesses, can not easily be removed. Instead of this, a preferable feature of the embodiment of FIG. 2 and its reference connection 114 and its working connection 115 is that the jacketing of the connections protrudes above the end surface of the cable connection piece 23, in order to reduce the likelihood of contamination of the connections. Of course, the geometry of the connections of FIG. 2 can be introduced into the embodiment of FIG. 1, and vice versa. Equally, other geometries may be chosen, such as e.g. a planar surface without protrusions or recesses. For protecting the connections 14 and 15 in the example of an embodiment according to FIG. 1, a barrier 9 is provided, which is arranged on the end face of the cable connection piece 13 between the replenishment opening 16 and the recesses for the connections 14 and 15, in order to reduce the possibility of contamination.

The example of an embodiment shown in FIG. 2 differs from the example of FIG. 1, aside from the already discussed embodiment of the connections, additionally in the fact that the electrolyte line 25 of the plug head aligns not with the end face of the complementary cable connection piece 23, but, instead, is skirted in the axial direction around the end face of the cable connection piece 23, by being displaced radially outwards therefrom. The sensor-near end of the electrolyte line 25 is preferably flexible and elastic, so that it can be connected to the replenishment opening 10 in the lateral surface of the outer shell 2. Preferably, measures are taken for providing pressure equalization between the reference container and the surroundings, as such were discussed above in connection with the example of an embodiment presented in FIG. 1, so that no further discussion thereof is required here.

The example of an embodiment shown in FIG. 2 has the advantage that a plug head 24 embodied to fit with pH-electrodes of the state of the art can be used, in order to enable servicing thereof over greater distances.

Finally, FIG. 3 shows, in contrast to FIG. 1, an example of an embodiment, in which there are no galvanic contacts at the interface between the cable connection piece 26 and the plug head 27. To this end, the pH-electrode has in its cable connection piece 26 a first converter 28, at whose sensor-near input the working electrode 6 and the reference electrode 7 are connected. The plug-head-near input, or output, as the case may be, of the first converter 28 is connected with an induction coil 30 in the induction plug 29. The induction plug 29 engages in a complementary induction sleeve 32 in the plug head 27, when the plug head is plugged onto the cable connection piece 26. The induction sleeve 32 is surrounded by an induction coil 33, which is embedded in the plug head 27 and connected with the coil-near output of a second converter 31, which, for example, is connected via a two-wire line 34, 35 (4–20 milliamperes). The power supply to the first converter 28 of the pH-electrode occurs via an alternating current, or AC, signal, which is produced by the converter 31 in the plug head 27 and coupled out via the induction coil 33. A load-modulation of the AC-signal by the converter 28 is used for transferring, or transmitting, the pH-dependent measurement signal. Optionally, converter 28 contains a memory element, in which, for example, calibration data of the pH-electrode or the fill dates for the reference container are stored. The writing and reading of the memory is done, likewise, by modulation, or load modulation, of the AC-signal, with the data being exchanged between the plug head 27 and a superordinated station, for example, by means of the Hart protocol or one of the other current standards used in laboratory, or process automation, technology.

The example of an embodiment illustrated in FIG. 3 is certainly the most complex; however, the advantage is that the inductive in- and out-coupling of data completely eliminates any corrosion problems and the associated device failure and inaccuracy of measurement data.

The plug heads of the invention are not only suited for conventional potentiometric sensors, but, equally, for more modern potentiometric sensors based on ion-sensitive, field-effect transistors, so-called ISFETs or ChemFETs.

The invention claimed is:

1. An apparatus, comprising;
a potentiometric sensor; and
a sensor plug head for connection to said potentiometric sensor, wherein:
said potentiometric sensor comprises:
a working electrode and a reference electrode, for providing a potential difference between said working electrode and said reference electrode, wherein the reference electrode is arranged in a reference electrolyte provided in a liquid container;
a connection piece for receiving said sensor plug head, said connection piece being mounted to said working electrode and said reference electrode; and
at least one output for issuing a potential-dependent signal, said signal depending on said potential difference, said output being provided at said connection piece; and
said sensor plug head comprises:
at least one input for receiving said potential-dependent signal from said output; wherein said output and said input each comprise an inductive interface, said potential-dependent-signal being issued by modulation of an AC-signal; and
a supply connection element for connecting to the liquid container in order to provide said liquid container with said reference electrolyte.

2. The apparatus as claimed in claim 1, wherein:
the sensor is a potentiometric sensor with an output for issuing a potential-dependent signal; and
the liquid container is a reference container.

3. The apparatus as claimed in claim 1, wherein:
said supply connection element includes a first connection element;
the sensor includes a second connection element; and
said first connection element is complementary to said second connection element.

4. The apparatus as claimed in claim 3, wherein:
said first connection element includes an electrolyte line and said second connection element includes an opening; and
said electrolyte line is connectable to said opening, for supplying the reference container with electrolyte.

5. The apparatus as claimed in claim 1, wherein:
said at least one output and said at least one input include galvanic contacts.

6. The apparatus as claimed in claim 1, wherein:
said potentiometric sensor is a pH-sensor or a redox sensor.

7. The apparatus as claimed in claim 1, wherein:
said potentiometric sensor includes an ion-sensitive field-effect transistor.

* * * * *